United States Patent

Staples

[11] Patent Number: 5,904,479
[45] Date of Patent: May 18, 1999

[54] ORTHODONTIC PALATE EXPANDER APPARATUS

[76] Inventor: Jeffrey J. Staples, 27185 Delemos, Mission Viejo, Calif. 92692

[21] Appl. No.: 07/975,422

[22] Filed: Nov. 12, 1992

[51] Int. Cl.[6] .................................................... A61C 7/00
[52] U.S. Cl. ................................................................ 433/7
[58] Field of Search .......................................... 433/7, 18, 6

[56] References Cited

U.S. PATENT DOCUMENTS

| | | |
|---|---|---|
| 3,800,420 | 4/1974 | Ouaknine . |
| 4,507,084 | 3/1985 | Blechmann et al. .................. 433/7 |
| 5,066,224 | 11/1991 | Block et al. . |

FOREIGN PATENT DOCUMENTS

| | | | |
|---|---|---|---|
| 608537 | 11/1960 | Canada ..................................... 433/7 |
| 608117 | 9/1960 | Italy ........................................... 433/7 |

OTHER PUBLICATIONS

Expansion Screws, Perfect in form, Function and Finish (Advertisement).
Expansion Screws (specification sheet fron dental supply catalog.
Designs and Applications of Palatal Expansion Appliances JCO/Apr., 1992, vol. XXVI, No. 4.

Primary Examiner—Cary E. O'Connor
Attorney, Agent, or Firm—Howard R. Lambert; Walter A. Hackler

[57] ABSTRACT

An orthodontic palate expander apparatus comprises an expansion screw assembly having first and second side plates with a threaded member connected between the plates so that its rotation in a first rotational direction about its longitudinal axis causes the plates to move away from one another in a palate expanding manner and rotation of it in the opposite direction causes the side plates to move toward one another for adjustment of the apparatus. A first gear is fixed to central regions of the threaded member and a second gear is mounted in driving relationship therewith. Manual rotation of the second gear thus causes rotation of the threaded member to thereby move the plates toward or away from each other according to the direction in which the second gear is rotated. The second gear is oriented so that with the apparatus installed in a patient's palate portions of the second gear are accessible through the patient's open mouth for turning the gear, for example, with an Allen wrench or screwdriver. The apparatus includes palate pads molded around the side plates or open frames that are joined to the plates, either of which transmit palate-widening forces to the palate. Metal retainers or bands are connected to outer regions of the palate pads or frames for attaching the apparatus to the patient's teeth to hold the apparatus in place. Instead of tooth retainers, outer ends of the frames are shaped closely to the patient's teeth and (in use) are bonded together as a unit for transmitting palate widening pressure to the patient's teeth.

23 Claims, 4 Drawing Sheets

ORTHODONTIC PALATE EXPANDER APPARATUS

BACKGROUND OF THE INVENTION

1. Field of the Invention

The present invention relates generally to the field of orthodontics and, more particularly, to cemented-types of palate expander apparatus and related expander screws used for widening the palate of dental patients, especially, young dental patients.

2. Background Discussion

Orthodontia procedures are commonly used for widening, that is, expanding, excessively narrow palates (upper jaws) of dental patients, especially young patients, whose palates still retain some plasticity or malleability. The understanding of the present inventor is, for example, that such palate expansion procedures—which are performed to permit patients to breathe more easily and/or to improve dental malocclusions and/or facial appearance—are performed in the United States at a rate of approximately five hundred per day or about one hundred twenty-five thousand per year.

The orthodontia procedure of palate expansion (i.e., the widening of the upper jaw) of individuals appears to have been first described in about 1860 by E. C. Angell. As historically described, the Angell dental appliance included a jackscrew assembly (now referred to as an expansion screw assembly) having joined thereto a pair of palate-engaging "collars." In use, the appliance was wedged in place in the roof of a patient's mouth with the collars bearing against the patient's opposing bicuspid teeth. The jackscrew of the appliance was described as then being actuated by a "notched dime" in a manner causing the attached collars to be moved apart so as to exert a sidewardly-directed force on the teeth against which the collars pressed. To achieve palate widening, the jackscrew was actuated in small increments of rotation over a period of several weeks such that the wearer's palate was gradually widened by a total of about four to seven millimeters without undue patient discomfort. After the desired palate expansion was attained and stabilized, the jackscrew was re-rotated to loosen the appliance enough so that it could be removed from the patient's palate.

It is significant to note that most orthodontic palate expanders presently used in the dental profession are modeled after the Angell palate expander. In this respect, many modern palate expander apparatus comprise a jackscrew assembly (which is an off-the-shelf item procured from dental supply companies) to which custom-fitted palate blocks or pads are connected through left-hand and right-hand threaded plates which form part of the jackscrew assembly. Other modern types of palate expanders are constructed with a metal framework joined to the jackscrew assembly and terminating in tooth bands soldered to the framework. Expansion of the jackscrew moves opposite side portions of the framework apart and exert palate-widening pressure on the palate through the tooth bands. In still other versions, the metal framework joined to the jackscrew assembly is configured such that no tooth bands are used.

The particular type of palate expander apparatus used by an orthodontist depends upon such factors as the shape of the patient's palate, the amount of palate expansion to be achieved and upon the orthodontists experience and preference. However, all of these versions of palate expanders use the same basic type of jackscrew expansion screw which is operated in a common manner.

One improvement to the Angell palate expander appliances that instead of operating the jackscrew by a "notched dime" (as described by Angell) modern palate expanders utilize a stiff, key-shaped stainless steel wire or pin, called an activation key. In operation, this key is inserted into a hole formed through central regions of the jackscrew and turns the jackscrew in windlass fashion. Because of clearance restrictions—both of the expansion screw assembly and the patient's palate after installation of the apparatus—the arcuate travel of the activation key is limited to only about a quarter turn of the jackscrew (that is, the key can only be pushed from the front of the patient's mouth through about ninety degrees towards the patient's throat) For further turning of the jackscrew, the key has to be removed and reinserted into an adjacent jackscrew hole and the key has to be pushed through the same front-to-rear, ninety degree arc. At least partly because the activation key is restricted to such limited rotational movement, present jackscrew assemblies are constructed so that a quarter rotation of the jackscrew is ordinarily all that is required for any single incremental palate widening step.

Notwithstanding the universal use of such expansion screw assemblies for the construction of palate expander apparatus by orthodontists, this type of expansion screw is difficult to use. To fully understand this difficulty, it is necessary to appreciate that the jackscrews used in expansion screw assemblies are very small. Typically, the jack screws are no longer than about 11 or 12 millimeters and the diameter of the central region of the jackscrew, through which the holes for the activation key are formed is typically only about 3 millimeters, the holes being only about 1 millimeter in diameter. The activation key itself is only about 20–25 millimeters in length. Thus, with the palate expander positioned across a patient's palate and arched along the palate, the insertion of the tip of the small key into the obscure, small keyhole in the jackscrew is very difficult. Moreover, once the key is in the jackscrew keyhole, the key must be pushed fully to the rear of the patient's mouth to properly expose the adjacent jackscrew keyhole for the subsequent key engagement. In pushing the small key toward the patient's throat and in then pulling the key from the jackscrew keyhole, there is a risk of dropping the key down the patient's throat—a key accidentally dropped into a patient's throat and entering one of the patient's lungs constitutes a serious medical emergency. For this reason, one end of a string is ordinarily attached to the key, the other end being formed into a finger loop for the adjustor; nevertheless, several occasions of a key being dropped down a patient's throat have been reported.

A substantial problem associated with the above-described manner in which heretofore available expansion jackscrews are adjusted by a small wire key can be further understood by considering that the frequent adjustment—which may be as often as twice a day—of the palate expander jackscrew in a patient's mouth is necessarily performed by other than the installing orthodontist or his or her staff.

Considering that palate expander apparatus are ordinarily installed only in children between the ages of about six to fourteen years of age, the individuals responsible for the frequent actuation of the jackscrew are ordinarily the child's parents (or guardians). Although instructed in technique, usually by a dental technician, it is, for example, often difficult for patents to properly adjust the jackscrew by use of the wire key. There may be a fear of hurting the child and the child may be apprehensive and may not be a willing patient. Furthermore, a woman's long fingernails may increase the difficulty of holding and pushing the key, and a man may have difficulty in manipulating the small key, especially if he has large fingers and/or is unaccustomed to such relatively delicate and painstaking tasks. Still further, the child's mouth is usually small and has limited access with restricted visibility of the jackscrew to be actuated. Even further, the force required to push the key against the jackscrew's resistance to turning can cause the key to bend and pull out of the jackscrew and/or slip out of the operator's fingers. Such action can cause injury to the patient's mouth or the operator's fingers. Also, as above mentioned, at the extreme of travel, the key must be removed from the jackscrew keyhole very carefully so as not to be dropped down the patient's throat.

It can be appreciated that the orthodontist's initial adjustment of the jackscrew in the above-described manner to fit the palate expander to the patient's palate is made more difficult and potentially unsafe for both the patient and the orthodontist by the current AIDS situation. As a result of concern for both patient and doctor infection of the AIDS virus, most practitioners wear or are required to wear surgical gloves when working in a patients mouth, particularly if there is a possibility of any patient-doctor blood contact. The wearing of surgical gloves can make manipulation of the actuation key more difficult and thereby increase the risk of injury to the patient's mouth or the orthodontists fingers and resulting bleeding.

U.S. Pat. No. 3,800,420 to Gilbert Ouaknine discloses the use of a rack and pinion-type expansion screw assembly for use in palate expander apparatus and is addressed to certain potential problems associated with the use of a jackscrew-type of expansion screw. Nevertheless, such patent does not address the above-described problems that relate to the necessity of using a pin-type key to adjust the expansion screw. Consequently, so far as is known to the present inventor, the type of palate expander apparatus disclosed in the Ouaknine patent has never been commercialized.

For these and other reasons, practical improvements to presently available expansion screw devices are needed to make them easier and safer to use, and it is the intent of the present invention to provide such an improved expansion screw assembly and palate expansion apparatus for which adjustment of the expansion screw assembly can be easily performed with the fingers outside of the patient's mouth by the use of a conventional Allen wrench, screwdriver or the like.

SUMMARY OF THE INVENTION

In accordance with the present invention, there is provided an orthodontia palate expander apparatus for causing the widening of a patient's palate. The palate expander apparatus comprises an expansion screw assembly which includes first and second side plates and a threaded screw member mounted for interconnecting the first and second side plates through threaded holes in the plates. The screw member is configured with left-and right-hand threads and is threaded through the side plates so that rotation of the member in a first rotational direction about its longitudinal axis causes the plates to move away from each other and so that rotation of the member in the opposite direction about causes the side plates to move toward each other.

The expansion screw assembly further includes gear means operatively connected to the threaded screw member for enabling selective manual rotation thereof in either the first or second direction according to whether it is desired to move the side plates farther apart or closer together. The gear means include a first gear fixed to the screw member so as to rotate with the member around its longitudinal axis and a second gear mounted in driving relationship with the first gear. Means are associated with the second gear for enabling manual rotation thereof in either rotational direction about its rotational axis by use of a common screwdriver, Allen wrench or the like, the rotational axis of the second gear being inclined forwardly and downwardly when the palate expander is installed in a patient's mouth so that the means for manual rotation of the second gear is readily accessible through the patient's open mouth with the operator's fingers outside of the patient's mouth.

In one embodiment of the invention, first and second palate pads or blocks are joined to, or molded around, respective ones of the first and second plates, the pads being sized and shaped to bear against side regions of a patient's palate when the apparatus is installed in a patient's mouth and the screw member is rotated in the first rotational direction the pads exert a palate-widening pressure against the palate.

Alternatively, instead of palate pads being attached to the expansion screw assembly, proximal ends of slender pins or rods forming an open framework are attached to each side plate of the expansion screw assembly open framework. Distal ends of the pins may have fixed thereto tooth bands or wires that are shaped to conform to the inward facing contour of several adjacent teeth against which the wires bear.

The expansion screw assembly of the palate expander apparatus preferably includes at least one guide or stabilizing pin that interconnects the first and second plates, an end region of pin being slidingly disposed through at least one of the side plates. The pin, which is installed so as to be parallel to the longitudinal axis of the threaded member, maintains the two side plates parallel to each other and prevents relative twisting between the side plates. In the case of palate expander apparatus constructed having an open framework of pins fixed to the expansion screw assembly, portions of the pins forming the framework may extend between the side plates and function to stabilize the two plates relative to one another.

In accordance with a preferred embodiment of the invention, the rotational axis of the second gear of the expansion screw assembly is orthogonal to the longitudinal axis of the threaded member, and although any gearing arrangement can be used, the second gear is preferably a worm gear, the first gear preferably being either an edge or a face gear. Alternatively, both of the first and second gears may be beveled gears.

A closed housing is preferably provided for enclosing the first and second gears and the related part of the screw member.

In order to retain the palate pad-type of palate expander apparatus in a patient's mouth, it is preferred, and may be required, that the apparatus include a first tooth band connected to outer regions of the first pad and a second tooth band connected to outer regions of the second pad, each of the bands being sized and configured for encircling at least one of the patient's teeth on each side of the palate. Upon installation of the palate expander apparatus, the bands may be cemented to the teeth they encircle. In the case of the open framework-type of palate expansion apparatus, the distal ends of each of the pins forming the framework have attached thereto a tooth band such that palate widening pressure is transmitted to four of the patient's teeth.

Because the completed construction of the palate expander apparatus has to be customized to a patient in whose mouth the apparatus is to be installed, the forming of the pads (or open framework rods) and tooth bands (or tooth-bearing wires) is necessarily done by the orthodontist installing the apparatus. The expansion screw assembly would, however, normally be an "off-the-shelf" device that would be purchased by orthodontists from suppliers of dental products and hardware. Consequently, the present invention separately covers the expansion screw assembly as well as the entire palate expander apparatus.

As such, an expansion screw assembly is provided that comprises the first and second side plates and the threaded screw member mounted for interconnecting the first and second side plates through threaded holes in the plates. The screw member is configured with left- and right-hand threads and is threaded through the side plates so that rotation of the member in a first rotational direction about its longitudinal axis causes the plates to move away from each other and so that rotation of the member in the opposite direction about causes the side plates to move toward each other.

The expansion screw assembly further includes gear means operatively connected to the threaded screw member for enabling selective manual rotation thereof in either the first or second direction according to whether it is desired to move the side plates farther apart or closer together. The gear means include a first gear fixed to the screw member so as to rotate with the member around its longitudinal axis and a second gear mounted in driving relationship with the first gear. Means are associated with the second gear for enabling manual rotation thereof in either rotational direction about its rotational axis by use of a common screwdriver or Allen wrench, the rotational axis of the second gear being inclined relatively forwardly and downwardly so that when a palate expander apparatus constructed using the expander screw assembly is installed in a patient's mouth the means for manually rotating the second gear is readily accessible through the patient's open mouth without the operator having to put his or her fingers inside the patient's mouth.

The described palate expansion apparatus and associated expansion screw assembly is easily and safely adjustable by non-orthodontic personnel (e.g., a patient's parents) and minimizes the risk of injury to both the patient in whose mouth the apparatus is installed and the individual making adjustments to the apparatus to cause the desired palate expansion.

BRIEF DESCRIPTION OF THE DRAWINGS

The present invention can be more readily understood by a consideration of the following detailed description when taken in conjunction with the accompanying drawings, in which.

Unless otherwise specifically stated, in the various Figures identical elements and features are given the same reference number.

DETAILED DESCRIPTION OF THE INVENTION

Description of Prior Art—FIGS. 1–4

The present invention can better be understood by a brief consideration, in conjunction with FIGS. 1 through 4, of an exemplary prior art palate expander apparatus and expansion screw assembly of the type employing palate pads and tooth bands.

Figure 1:
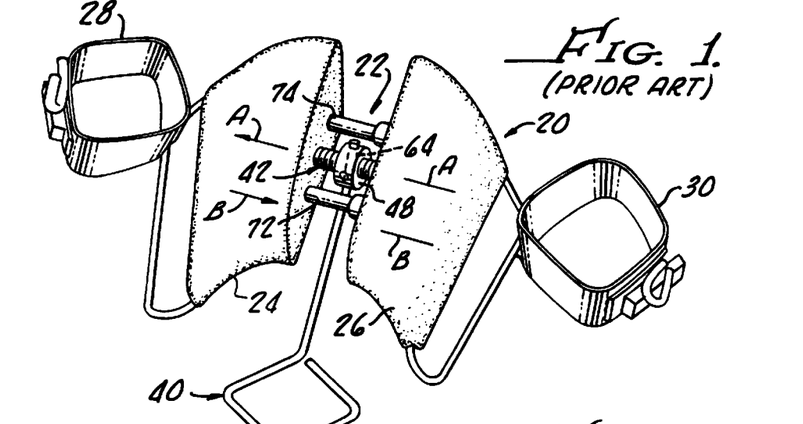
FIG. 1 is a perspective drawing of an exemplary prior art orthodontic palate expander apparatus of the palate block or pad type, showing first and second palate-bearing pads and an interconnecting jackscrew assembly for causing the pads to be pushed apart for applying pressure to inner-side gum regions of a patient's palate and showing tooth bands fixed to the pads for retaining the apparatus in a patient's mouth, and further showing a prior art key used to turn the jackscrew to move the two pads farther apart from one another to cause the palate expansion and for moving the two pads back toward one another as may be needed for adjusting the apparatus.

Accordingly, FIG. 1 depicts an exemplary palate pad-type of palate expander apparatus 20 for purposes of illustrating the invention. However, as described below, other types of palate expander apparatus constructed with open framework means comprising pins fixed to a central expansion screw assembly are also covered by the present invention.

Figure 2:
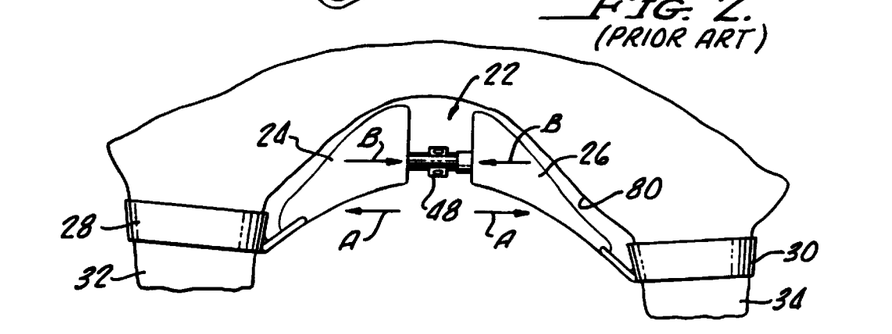
FIG. 2 is a front elevational view of the prior art palate expander apparatus of FIG. 1 showing its manner of insertion and use in a patient's mouth.

More specifically, palate pad-type palate expansion apparatus 20 depicted in FIGS. 1–4, generally comprises an expansion screw assembly 22 and first and second palate pads or blocks 24 and 26 which are formed around side regions of the expansion screw assembly. Respective first and second retaining bands 28 and 30 are attached to end regions of associated ones of first and second palate pads 24 and 26 for attaching apparatus 20 to corresponding teeth 32 and 34 of a patient in whose mouth the apparatus is installed (FIG. 2). Palate pads 24 and 26 are generally custom formed of plastic in accordance with well known dental procedures, such as by taking the impression of the intended patient's palate and upper jaw. Apparatus retaining bands, which are ordinarily formed of surgical stainless steel, are shaped to fit closely around upper molars of the intended patient.

An operating "tool" 40, shown in FIG. 1 as having been formed by the bending of a stiff wire into a key-like shape, is provided for operating expansion screw assembly 22 to selectively cause palate pads 24 and 26 to move away from each other (direction of Arrows "A") for causing palate expansion or to cause the palate pads to move toward each other (direction of Arrows "B") for adjustment of apparatus 20 in the event that the apparatus is inadvertently adjusted too tightly in a patient's mouth (FIGS. 1 and 2).

Figure 3:
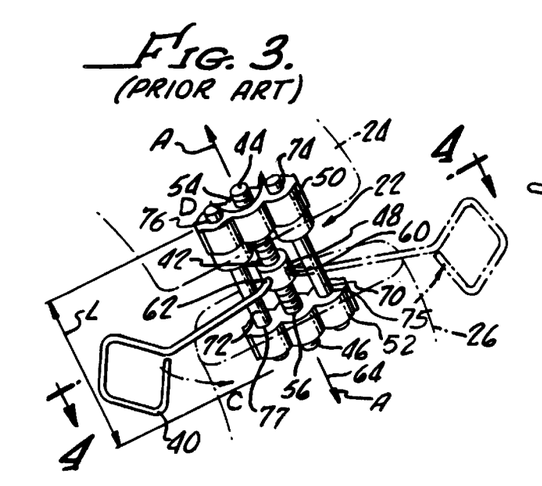
FIG. 3 is a perspective drawing of the expander screw portion of the palate expander apparatus of FIGS. 1 and 2 showing first and second side plates around which the pads are molded, a jackscrew with left- and right-hand screw threaded end regions interconnecting the side plates, and showing a pair of guide or stabilizer pins connected between the side plates to stiffen the expander screw portion, and further showing operation of the jackscrew by the key (shown in FIG. 1) to move the side plates apart from one another.

As shown in FIG. 3, prior art expansion screw assembly 22, of the type that is commercially available from dental supply companies, comprises an elongate screw jack or screw member 42 formed having left-hand and right-hand threaded end regions 44 and 46 on either side of an enlarged diameter central region 48. Further comprising expansion screw assembly 22 are first and second rigid side plates 50 and 52 that are interconnected by jackscrew 42. For such purpose, jackscrew threaded end regions 44 and 46 are threadably received into central, mating, threaded apertures 54 and 56 of respective side plates 52 and 50.

Radial holes 60 are drilled through central region 48 of jackscrew 42 for receiving a tip region 62 of tool 40, whereby the jackscrew can be rotated in either rotational direction, about a longitudinal axis 64 according to whether it is desired to move side plates 50 and 52 away from or toward each other.

Figure 4:
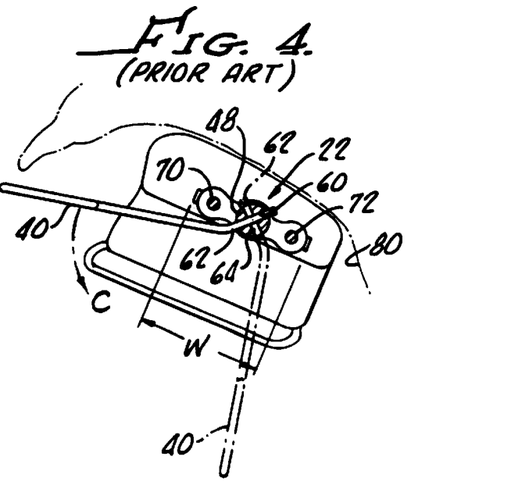
FIG. 4 is a transverse cross sectional drawing looking along line 4—4 of FIG. 3 showing operation of the prior art palate expander apparatus and further showing the manner of operating the apparatus in a patient's mouth to provide palate expansion (widening)

Typically stabilization of side plates 50 and 52—that is the prevention of relative rotation therebetween—is provided by first and second guide pins or rods 70 and 72. Such guide pins 70 and 72 are shown symmetrically mounted outboard of jackscrew 42 and are parallel to jackscrew axis 64 (FIGS. 3 and 4). Guide pin 70 slidingly extends through apertures 74 and 75 in respective side plates 50 and 52. In a similar manner, guide pin 72 slidingly extends through aperture 76 and 77 in respective side plates 50 and 52 (FIG. 3). Pins 70 and 74 may be free to slide out of side plates 50 and 52; alternative, for example, burrs (not shown) may be formed on end regions of the pins to restrain them from sliding out of the side plates.

Typical overall dimensions of expansion screw assembly 22 are width, W, about 8 to 10 mm (FIG. 4) and length, L, about 11 to 13 millimeters (FIG. 3). Expansions from fully retracted side plates 50 and 52 to their fully extended position (such as is shown in FIG. 3) is between about 5 to 7 millimeters.

The in situ operation of expansion screw assembly 22, and therefore of apparatus 20, is depicted in FIG. 4. With apparatus 20 installed in a patients mouth in a position beneath a lower surface 80 of the patients palate, end region 62 of tool 40 is inserted (through the patient's open mouth) into a closest one of apertures 60 through jackscrew central region 48. Tool 40 is then pushed rearwardly toward the patient's throat (direction of Arrow "C") as far as possible, thereby causing jackscrew 42 to partially rotate counterclockwise (direction of Arrow "D") as seen in FIG. 3, through about 90 degrees. Expansion screw assembly 22 is constructed so that each such quarter turn of jackscrew 42 moves side plates 50 and 52 about 0.8 millimeters further apart.

Description of FIGS. 5–9—Preferred Embodiment of Invention:

For descriptive purposes, elements and features of the preferred embodiment apparatus of FIGS. 5–9 that correspond to elements and features of above-described prior art apparatus 20 of FIGS. 1–4 are given the same reference number preceded by a "1."

Figure 5:
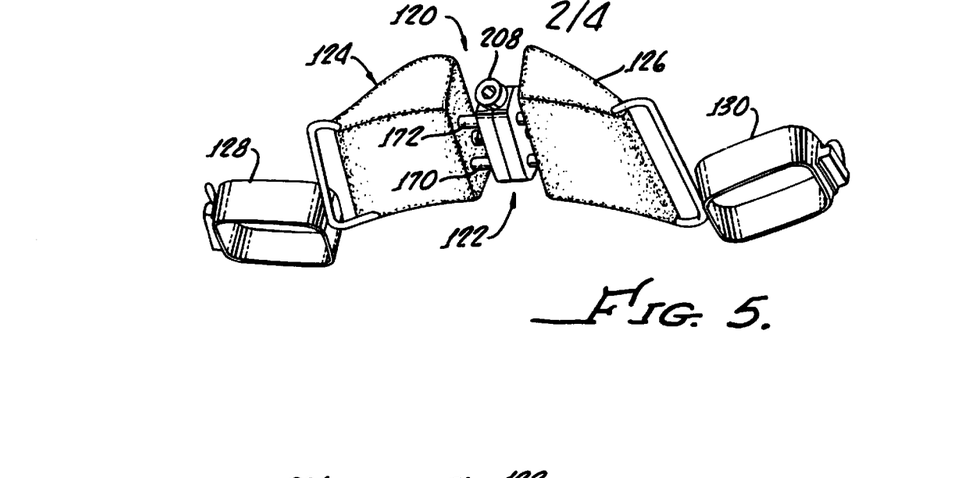
FIG. 5 is a perspective drawing similar to FIG. 1 showing an embodiment of the palate expander apparatus of the present invention, showing the palate-bearing pads and tooth bands and showing a housing on an expander screw portion in which gears for operating the jackscrew are housed.

FIG. 5 (which is similar to FIG. 1) depicts a palate expander apparatus 120 in accordance with a preferred embodiment of the present invention. Palate expander apparatus 120, which corresponds to above-described apparatus 20, comprises an expansion screw assembly 122 and respective first and second palate pads or blocks 124 and 126 having connected thereto respective tooth bands 128 and 130. Palate pads 124 and 126 directly correspond to, and perform the same function as, above-described palate blocks 24 and 26 and apparatus retaining bands 128 and 130 correspond directly to, and perform the same function as, above-described retaining bands 28 and 30.

Figure 6:
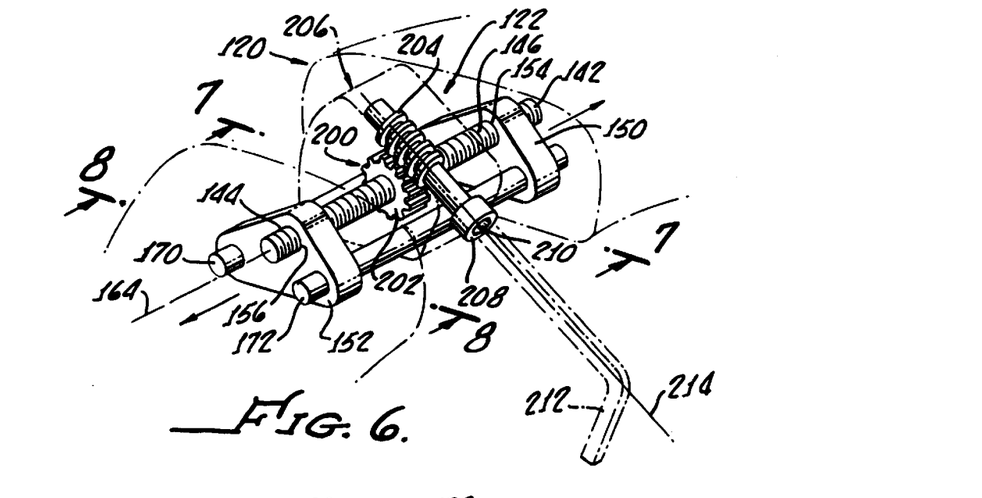
FIG. 6 is a perspective drawing similar to FIG. 3 showing the expander screw portion of the present embodiment of the invention having a first gear mounted to the jackscrew and a second gear in driving relationship therewith, the second gear being rotated, to cause rotation of the jackscrew, by a conventional Allen wrench and showing the housing of the expander screw portion in phantom lines.
Figure 7:
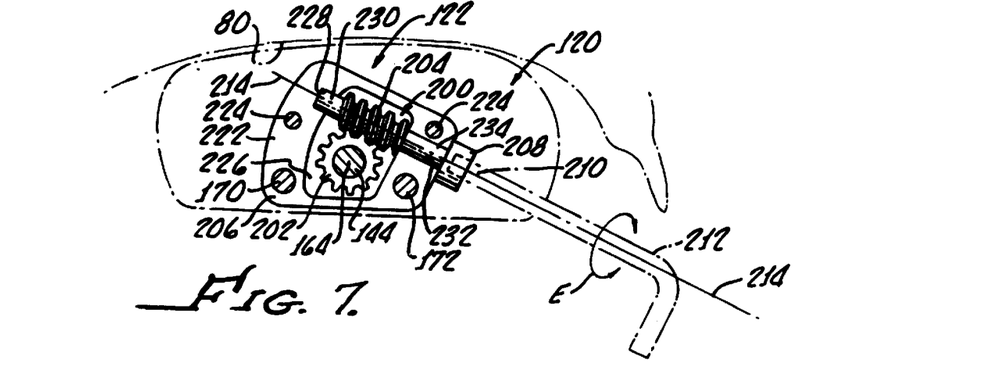
FIG. 7 is a longitudinal cross sectional drawing looking along line 7—7 of FIG. 6 showing the intermeshing of the first and second gears and showing the mounting of the second gear—a worm gear—in the housing and further, showing the manner of rotating the worm gear by means of an Allen wrench.
Figure 8:
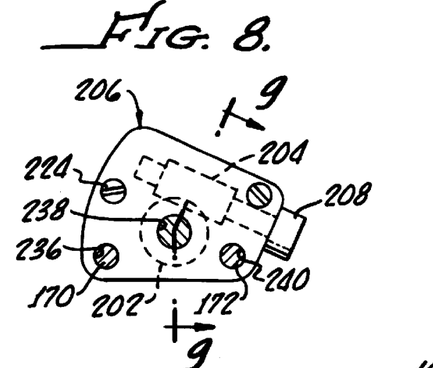
FIG. 8 is a longitudinal cross sectional drawing looking along line 8—8 of FIG. 6 showing one side of the housing of the expansion screw portion.

As shown in FIGS. 6–8, expansion screw 122 comprises a jackscrew 142 having left-hand and right-hand threaded end regions 144 and 146 and first and second side plates 150 and 152. Jackscrew 142 corresponds to above-described jackscrew 42 and side plates 150 and 152 correspond to above-described side plates 50 and 52. Threaded apertures 154 and 156 formed in respective first and second side plates 150 and 152 threadably receive corresponding left- and right-hand threaded end regions 144 and 146 of jackscrew 142. First and second guide pins 170 and 172, which correspond to above-described guide pins 70 and 72, interconnect side plates 150 and 152 in the manner described above for such guide pins 70 and 72.

Comprising an important part of expansion screw assembly 122 are gear means 200 for causing rotation of jackscrew 142 about its longitudinal axis 164. Comprising gear means 200 are a first gear 202 which is non-rotatably fixed to central regions of jackscrew 142 and a second gear 204 that is in mounted in a housing 206 so as to be in driving mesh with the first gear (FIG. 7). Preferably, as depicted in FIGS. 6 and 7, first gear 202 is a conventional circular gear and second gear 204 is an elongate worm or spiral gear.

Second gear 204 is formed having an exposed forward end region 208 with a recess 210 shaped for receiving a driving end of a conventional Allen wrench 212 (shown in phantom lines in FIGS. 6 and 7) by means of which the second gear is manually turned to cause, through first gear 202, the rotation of jackscrew 142. Second gear recess 210 may alternatively be shaped to receive the driving tip of a screwdriver, torquedriver or any other type of conventional (or specialized) driver.

A longitudinal axis 214 of second gear 204 is preferably orthogonal to jackscrew longitudinal axis 164, the second gear axis 214 being inclined downwardly and forwardly from the normal installation position of palate expander apparatus 120 shown in FIG. 7.

The inclination of second gear axis 214 is such as to enable an individual (other than the patient wearing palate expander apparatus) to easily insert the driving end of Allen wrench 212 (or the like) into second gear recess 210. In this regard, it will be appreciated that once Allen wrench 212 (or the like) is inserted into second gear recess 210, it is only required that the wrench be twisted in either axial direction about axis 214 in order to force associated end plates 150 and 152 apart for the purpose of causing palate expansion by apparatus 120 or to draw the end plates closer together to enable adjustment of such apparatus if it has been over tightened in a patient's mouth.

The thread size and pitch of first and second gears 202 and 204 are relatively selected so that a rotation of the second gear (by wrench 212) in the palate expanding direction causes a sideward expansion of apparatus 120 of about 0.8 millimeters. Such sideward expansion of apparatus 120 by the operation of gears 202 and 204 is consistent with a regimen of adjusting apparatus twice a day for a period of about 14 days for a maximum palate expansion of about 10 to 13 millimeters for any one apparatus.

As shown in FIGS. 6 and 7, guide pins 170 and 172 are parallel with longitudinal axis 164 of jackscrew 142. As best seen in FIG. 7, guide pins 170 and 172 and jackscrew 142 are arranged in a triangular relationship with the jackscrew being located above (relative to palate surface 80) the guide pins to thereby enable the appropriate inclination angle of second gear axis 214. If pins 170 and 172 were coplanar with jackscrew 142 (as is the case for pins 70 and 72 and jackscrew 42 of above-described, prior art palate expander apparatus 20), the appropriate angulation of second gear axis 214 would be difficult—but still possible—to attain. Alteratively, only a single guide pin, corresponding to first guide pin 170, could be used in expansion screw assembly 122 to enable appropriate angulation of second gear axis 214 while minimizing the size of the assembly.

Figure 9:
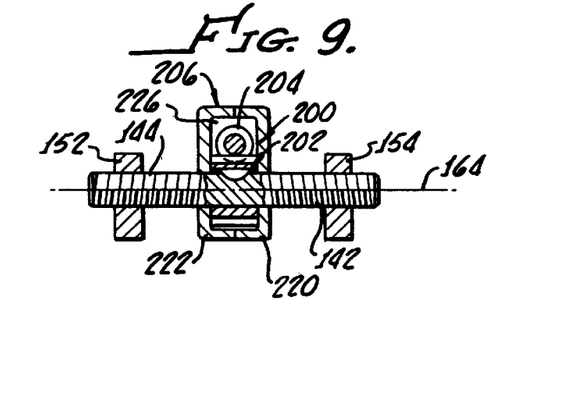
FIG. 9 is a transverse cross sectional drawing looking along line 9—9 of FIG. 8 showing further details of the expansion screw portion of the present palate expander apparatus.

Housing 206, as depicted in FIGS. 8 and 9, is formed of clamshell halves 220 and 222 which are held together by a plurality of screws 224. Alternatively, housing halves may be welded together to form a closed housing 206.

An open, internal region 226 of housing 206 encloses first gear 202 and related portions of screw member 142, as well as second gear 204 except for region 208 thereof. A housing recess 228 (FIG. 7) receives a distal end region 230 of second gear 204 and functions as a retainer and guide therefor. A cylindrical opening 232 in housing 206 in alignment with recess 228 serves to support and guide a necked-down region 234 of second gear 204. As shown in FIG. 8, stabilizing pins 170 and 172 and screw member 142 extend through respective apertures 236, 238 and 240 formed through housing 206.

Housing 206 may be constructed of a plastic or surgical grade of stainless steel and is preferably liquid tight so that bacteria-containing mouth fluids and fluids drunk by the patient cannot accumulate inside the housing and cause unpleasant odors and become a possible source for mouth infection.

Figure 10:
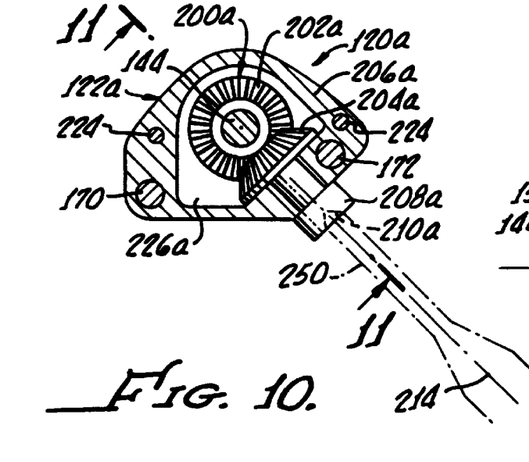
FIG. 10 is a longitudinal cross sectional drawing similar to FIG. 7 but showing a variation gear arrangement in which both the first and second gears are beveled gears.
Figure 11:
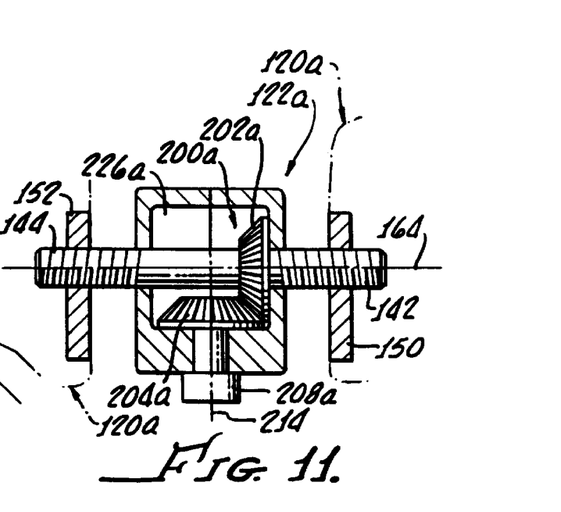
FIG. 11 is a transverse cross sectional drawing looking along line 10—10 of FIG. 9 showing another view of the variation expansion screw portion showing the intermeshing of the two beveled gears used to cause rotation of the jackscrew.

Variation Expansion Screw Assembly of FIGS. 10 and 11:

There is depicted in FIGS. 10 and 11 a variation palate expander apparatus 120a which is in all respects except for the configuration of first and second gears 202a and 204a and the related size and shape of housing 206a and gear-receiving housing recess 226a identical to above-described palate expander apparatus 120. In such FIGS. 10 and 11, elements and features identical to those described for FIGS. 5 through 9 are given the same reference number; similar elements and features are given the same reference number as used in conjunction with the description of apparatus 120 followed by an "a."

As shown in FIGS. 10 and 11, both first and second gears 202a and 204a (which form gear means 200a) are bevel gears which are intermeshed so that the rotation of the second gear causes rotation of the first gear, with consequent rotation of screw member 144 to which the first gear is fixed. Because of the different shape of gears 202a and 204a (as compared to above-described gears 202 and 204) housing 206a is somewhat different is shape from corresponding housing 206, but is otherwise constructed in the above-described manner and may be assembled by screws 224, or may be welded closed.

By illustrative example, recess 210a of second gear 204a is shaped to receive the tip of a conventional screwdriver 250 (shown in phantom lines in FIG. 10) which may be of the slotted or Philips-head type. Alternatively, recess 210a may be configured to receive a torquedriver, or gear region 208a may be shaped to be turned by a conventional nut driver.

Angulation of second gear axis 214 is the same as that described above for axis 214 of second gear 204, head region 208a being thereby positioned for easy access through the patient's open mouth without the operator having to insert his or her fingers into the patient's mouth.

Figure 12:
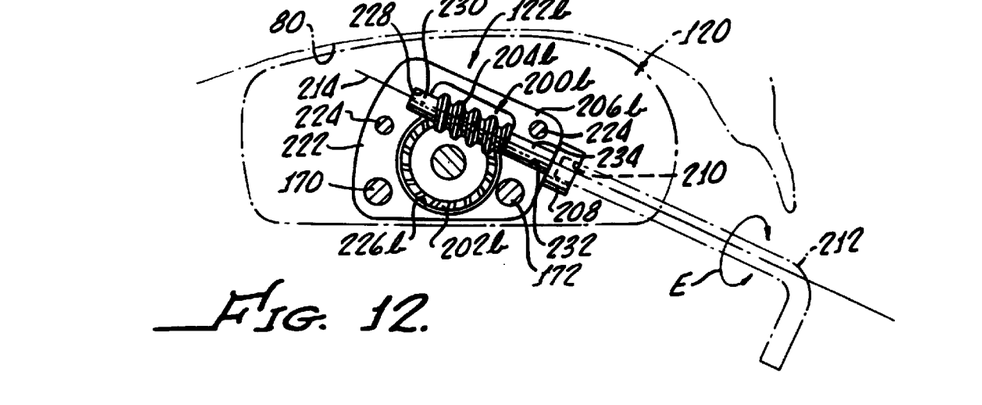
FIG. 12 is a second variation expansion screw assembly showing worm gear in driving relationship with a face gear that is fixed to the jackscrew portion of the expansion screw assembly.

Variation Expansion Screw Assembly of FIG. 12:

There is depicted in FIG. 12 a variation expansion screw assembly 122b that is similar to above-described expansion screw 122 except that first gear 202b (of gear means 200b), which corresponds to first gear 202, is shown as a face gear instead of an edge gear (as is first gear 202). Because face gear 202b is larger than edge gear 202, housing recess 226b is made larger than above-described housing recess 226, and housing 206b may, accordingly be somewhat larger than housing 206. In FIG. 12, elements and features identical to those described for expansion screw 122 are given the same reference number; similar elements and features are given the same reference number as used in conjunction with the description of apparatus 120 followed by an "b."

Figure 13:
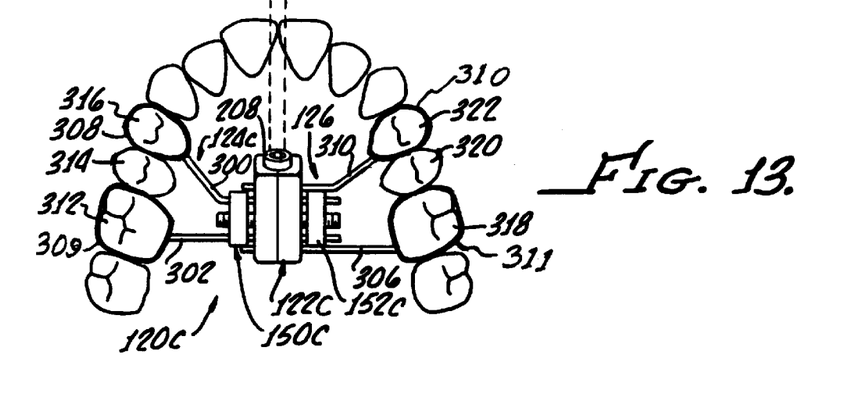
FIG. 13 is a perspective drawing of a variation palate expander apparatus showing the expansion screw assembly of the present invention having attached thereto first and second open framework means and corresponding first and second tooth band means attached to distal ends of the framework means for attaching the apparatus to the patient's teeth.

Variation Palate Expansion Apparatus of FIG. 13:

FIG. 13 depicts a variation palate expansion apparatus 120c that is similar to above-described palate expander apparatus 120 except that respective first and second open framework or pressure transferring means 124c and 126c are used in place of above-described palate pads 124 and 126 (FIG. 5). First framework means 126c comprises respective front and rear stiff pins 300 and 302 and second framework means comprises respective front and rear pins 304 and 306. Proximal (i.e., inboard) end regions of first pins 300 and 302 are fixed to a first side plate 150c (which corresponds to above-described first side plate 150) of expansion screw 122c (which is similar to above-described expansion screw assembly 122) and proximal ends of second pins 304 and 306 are fixed to a second side plate 152c (which corresponds to above-described second plate 152). The proximal ends of first pins 300 and 302 extend through apertures in second side plate 152c and thereby serve the same side plate stabilizing function as described above for pins 170 and 172.

As shown, respective first, second, third and fourth tooth bands 308, 309, 310 and 311 are fixed to distal (i.e., outboard) end of respective pins 300, 302 and 304, 306 for retaining palate expander apparatus 120c in a patient's mouth and for transmitting palate-widening forces to the patient's palate through respective teeth 316, 312, 322 and 318. First, second, third and fourth tooth bands 308, 309, 310 and 311 are similar in function to above-described first and second tooth bands 128 and 130 (FIG. 5).

Figure 14:
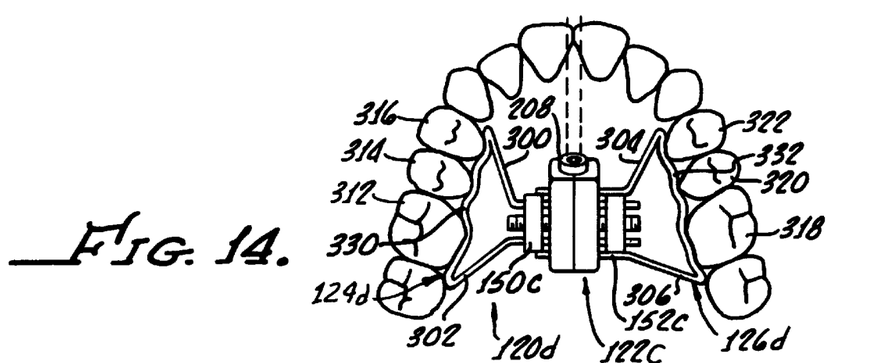
FIG. 14 is a perspective drawing of a second variation palate expander apparatus showing first and second framework means attached to the expansion screw assembly of the present invention and showing distal ends of each side of the framework interconnected to form a region shaped to conform closely to inward-facing sides of several teeth for transmitting palate widening pressure to the teeth.

Variation Palate Expansion Apparatus of FIG. 14:

Another variation palate expansion apparatus 120d of the open framework type is depicted in FIG. 14. Palate expansion apparatus 120d is similar to above-described palate expansion apparatus 120c except that distal ends of first pins 300 and 302 are interconnected and shaped, at a region 330, to fit closely against inward facing surfaces of a plurality of teeth, for example, teeth 312, 314 and 316. In a like manner, distal ends of second pins 304 and 306 are interconnected and shaped, at a region 332, to fit closely against inward facing surfaces of a plurality of teeth, for example, teeth 318, 320 and 322. Proximal ends of pins 300, 302, 304 and 306 are attached to expansion screw assembly 122c in the manner described above in relation to FIG. 13.

In a patient's mouth, a plastic adhesive is then placed over regions 330 and 332 and their respective teeth, thereby binding the pin regions and teeth together as one unit. This adhesive unit serves the same purpose as pins attached to tooth bands (e.g., bands 308, 309, 310 and 311, FIG. 13) in that expansive forces are transmitted through the teeth to the palate.

First pins 300 and 302 together comprise a first framework means 124d and second pins 304 and 306 form second framework means 126d.

It will, of course, be appreciated that any of above-described expansion screw assemblies 122, 122a or 122b (FIGS. 7, 10 and 12) may be used in either palate pad-type palate expansion apparatus (e.g., above-described apparatus 120) or open framework-type palate expansion apparatus (e.g., above-described apparatus 120c or 120d) as may be desired.

As is evident from the foregoing description, all of above-described expansion screw assemblies 122, 122a and 122b are easily actuated through the axial rotation of a conventional Allen wrench, screwdriver, torguedriver or the like and without the use of a shaped wire tool 40 such as is used in known prior art palate expander apparatus 20. Accordingly, the above-described palate expander apparatus of the present invention are much easier and safer to operate (as compared to known prior art palate expanders exemplified by apparatus 20) by either orthodontic professionals or non-professionals (e.g., parents of the patient in which the apparatus are installed).

Although there has been described and illustrated an improved palate expander apparatus and a variation thereof (together with variations of associated expansion screw assemblies) in accordance with the present invention for purposes of illustrating the manner in which the invention may be used to advantage, it is to be appreciated that the invention is not limited thereto. Therefore, any and all variations and modifications that may occur to those skilled in the dental and orthodontic arts are to be considered as being within the scope and spirit of the claims as appended hereto.

What is claimed is:

1. An orthodontia palate expander apparatus for causing the widening of a patient's palate, said palate expander apparatus comprising:

a. an expansion screw assembly which includes:

(1) first and second side plates;

(2) a threaded member mounted for interconnecting said first and second side plates, said threaded member being configured and connected to the side plates so that rotation of the member in a first rotational direction about a longitudinal axis thereof causes the plates to be moved away from one another and so that rotation of the member in a second, opposite direction about said axis causes the side plates to be moved toward one another; and         (3) gear means operatively connected to said threaded member for enabling selective manual rotation thereof in either the first or second direction according to whether it is desired to move the side plates farther apart or closer together, said gear means including a first gear fixed to said threaded member so as to rotate with the member around the longitudinal axis thereof and a second gear mounted in driving relationship with said first gear, said second gear including means for enabling manual rotation thereof in either rotational direction about its rotational axis by use of a common screwdriver or Allen wrench, said rotational axis being inclined forwardly and downwardly when a palate expander constructed from the expansion screw apparatus is installed in a patient's mouth so that said means for manual rotation is exposed through a patient's open mouth; and     b. first and second pressure transfer means joined to respective ones of said first and second plates, said pressure transfer means enabling pressure to be transferred to side regions of a patient's palate so that when the threaded member is rotated in said first rotational direction the pressure transfer means are caused to exert a palate-widening pressure against said palate.

2. The orthodontia palate expander apparatus as claimed in claim 1, wherein the expansion screw assembly includes at least one stabilizing pin interconnecting said first and second plates and having an end region slidingly disposed through at least one of the side plates, a longitudinal axis of said at least one stabilizing pin being parallel to the longitudinal axis of said threaded member.

3. The orthodontia palate expander apparatus claimed in claim 1, wherein said second gear of the expansion screw assembly is mounted on a rotational axis that is orthogonal to the longitudinal axis of the threaded member.

4. The orthodontia palate expander apparatus as claimed in claim 1, wherein said second gear is a worm gear.

5. The orthodontia palate expander apparatus as claimed in claim 1, wherein each of said first and second gears is a beveled gear.

6. The orthodontia palate expander apparatus as claimed in claim 1, including a housing in which said first and second gears are mounted, said housing also enclosing central regions of said threaded member.

7. The orthodontia palate expander apparatus as claimed in claim 1, wherein said first and second pressure transfer means include respective first and second pressure pads.

8. The orthodontia palate expander apparatus as claimed in claim 7, including a first band connected to outer regions of said first pad and a second band connected to outer regions of said second pad, each of said first and second bands being sized and configured for encircling at least one tooth of a patient with which the apparatus is being used to thereby positively retain the apparatus in the patient's mouth.

9. The orthodontia palate expander apparatus as claimed in claim 1, wherein said first and second pressure transfer means include respective first and second open frames.

10. The orthodontia palate expander apparatus as claimed in claim 9, including first tooth band means connected to outer regions of said first open frame and second tooth band means connected to outer regions of said second open frame, each of said first and second tooth band means being configured for encircling a plurality of teeth of a patient with which the apparatus is being used to thereby positively retain the apparatus in the patient's mouth.

11. An expansion screw apparatus for use in constructing an orthopedic palate expander for causing the widening of a patient's palate, said expansion screw apparatus comprising:

a. first and second side plates, each of said side plates being configured for having attached or molded thereto associated pads for bearing against side regions of a patient's palate;

b. a threaded member mounted for interconnecting said first and second side plates, said threaded member being configured and connected to the side plates so that rotation of the member in a first rotational direction about a longitudinal axis thereof causes the plates to be moved away from one another, for achieving palate expansion, and so that rotation of the member in a second, opposite direction about said axis causes the side plates to be moved toward one another;

c. at least one stabilizing pin disposed between said first and second plates and having an end region slidingly disposed through at least one of the side plates, a longitudinal axis of said pin being parallel to the longitudinal axis of said threaded member; and d. gear means operatively connected to said threaded member for enabling selective manual rotation thereof in either the first or second direction according to whether it is desired to move the side plates farther apart or closer together, said gear means including a first gear fixed to said threaded member so as to rotate with the member around the longitudinal axis thereof and a second gear mounted in driving relationship with said first gear.

12. The expansion screw apparatus as claimed in claim 11, wherein said second gear is mounted on a rotational axis that is orthogonal to the longitudinal axis of the threaded member.

13. The expansion screw apparatus as claimed in claim 11, wherein said second gear includes means for enabling manual rotation thereof in either rotational direction about a rotational axis by use of a common screwdriver or Allen wrench, said rotational axis being inclined forwardly and downwardly when a palate expander constructed from the expansion screw apparatus is installed in a patient's mouth so that said means for manual rotation is exposed through a patient's open mouth.

14. The expansion screw apparatus as claimed in claim 11, wherein said second gear is a worm gear.

15. The expansion screw apparatus as claimed in claim 11, wherein each of said first and second gears is a beveled gear.

16. The expansion screw apparatus as claimed in claim 11, including a housing in which said first and second gears are mounted, said housing also enclosing central regions of said threaded member.

17. An expansion screw apparatus for use in constructing an orthopedic palate expander for causing the widening of a patient's palate, said expansion screw apparatus comprising:

a. first and second side plates, each of said side plates being configured for having attached or molded thereto associated pads for bearing against side regions of a patient's palate;

b. a threaded member mounted for interconnecting said first and second side plates, said threaded member being configured and connected to the side plates so that rotation of the member in a first rotational direction about a longitudinal axis thereof causes the plates to be moved away from one another, for achieving palate expansion, and so that rotation of the member in a second, opposite direction about said axis causes the side plates to be moved toward one another; and c. gear means operatively connected to said threaded member for enabling selective manual rotation thereof in either the first or second direction according to whether it is desired to move the side plates farther apart or closer together, said gear means including a first gear fixed to said threaded member so as to rotate with the member around the longitudinal axis thereof and a second gear mounted in driving relationship with said first gear, said second gear including means for enabling manual rotation thereof in either rotational direction about its rotational axis by use of a common screwdriver or Allen wrench, said rotational axis being inclined forwardly and downwardly when a palate expander constructed from the expansion screw apparatus is installed in a patient's mouth so that said means for manual rotation is exposed through a patient's open mouth.

18. The expansion screw apparatus as claimed in claim 17, including one or more stabilizing pins interconnecting said first and second plates and having an end region slidingly disposed through at least one of the side plates, a longitudinal axis of said one or more rods being parallel to the longitudinal axis of said threaded member.

19. The expansion screw apparatus as claimed in claim 17, wherein said second gear is mounted on a rotational axis that is orthogonal to the longitudinal axis of the threaded member.

20. The expansion screw apparatus as claimed in claim 17, wherein said second gear is a worm gear.

21. The expansion screw apparatus as claimed in claim 17, wherein each of said first and second gears is a beveled gear.

22. The expansion screw apparatus as claimed in claim 17, including a housing in which said first and second gears are mounted, said housing also enclosing central regions of said threaded member.

23. An orthodontia palate expander apparatus for causing the widening of a patient's palate comprising:

an expansion screw assembly which includes:
      a threaded member having a longitudinal axis;
      two bodies meshed with said threaded member, said bodies being movable in opposite directions along said threaded member upon rotation of said threaded member;
   first and second means for transferring pressure to side regions of a patient's palate, said first transferring means joined to one body and said second transferring means joined to the other body;
   the improvement comprising:
      gear means operatively connected to said threaded member for enabling selective manual rotation thereof, said gear means including a first gear fixed to said threaded member and a second gear mounted in driving relationship with the first gear, said second gear including means for enabling manual rotation thereof.

* * * * *